US006246915B1

(12) United States Patent
Boutos

(10) Patent No.: US 6,246,915 B1
(45) Date of Patent: Jun. 12, 2001

(54) APPARATUS FOR STIMULATING LIVING TISSUE

(76) Inventor: David Boutos, 4420 Dunlap Crossing St., Las Vegas, NV (US) 89129

( * ) Notice: Subject to any disclaimer, the term of this patent is extended or adjusted under 35 U.S.C. 154(b) by 0 days.

(21) Appl. No.: 09/212,446

(22) Filed: Dec. 16, 1998

(51) Int. Cl.$^7$ ...................................................... A61N 1/04
(52) U.S. Cl. ........................... 607/143; 607/138; 607/115; 607/39
(58) Field of Search .................................... 607/138, 152, 607/143, 115, 116, 142, 140, 149, 39; 600/372, 373, 394, 393

(56) References Cited

U.S. PATENT DOCUMENTS

| | | | | |
|---|---|---|---|---|
| 3,279,468 | * | 10/1966 | Le Vine | 607/140 |
| 3,566,860 | * | 3/1971 | Moe, Jr. | 600/394 |
| 4,911,657 | * | 3/1990 | Berlin | 600/394 |
| 5,306,236 | * | 4/1994 | Blumenfeld et al. | 607/116 |
| 5,571,118 | * | 11/1996 | Boutos | 607/143 |
| 5,697,966 | * | 12/1997 | Boutos | 607/138 |
| 5,782,902 | * | 7/1998 | Boutos | 607/143 |
| 5,928,142 | * | 7/1999 | Cartmell et al. | 607/152 |
| 5,978,693 | * | 11/1999 | Hamilton et al. | 600/394 |
| 6,064,901 | * | 5/2000 | Cartmell et al. | 607/149 |

\* cited by examiner

*Primary Examiner*—Kennedy Schaetzle
(74) *Attorney, Agent, or Firm*—Jordan M. Meschkow; Lowell W. Gresham; Meschkow & Gresham, P.L.C.

(57) ABSTRACT

Electrodes for stimulating living tissue such as penile, scrotal, anal, vaginal, and clitoral tissue are shown. Electrical stimulation to such areas is intended to induce penile erection, or to induce excitation and orgasm in either males or females, particularly where impotence or frigidity is a problem. Four embodiments of the electrode apparatus include a flexible base and an electrode removably coupled to the base. The electrode is formed from elastomeric material and can be optionally formed into a loop for use around penile or scrotal tissue and against vaginal or anal issue. In addition, two embodiments include a penile sheath for secure placement and retention of the electrode on the penis. An electrical contact at one end of the electrode allows the electrode to be connected to an electrical source.

17 Claims, 6 Drawing Sheets

APPARATUS FOR STIMULATING LIVING TISSUE

TECHNICAL FIELD OF THE INVENTION

The invention relates to devices for applying electrical energy to living tissue. More particularly, the present invention relates to an apparatus for electrically stimulating penile, scrotal, anal, vaginal, and clitoral tissue.

BACKGROUND OF THE INVENTION

It is known that medical disorders such as diabetes, leukemia, anemia, X-ray exposure, and so forth can cause impotence in males and frigidity in females. Furthermore, it is known that the application of electrical stimulation to penile tissue can cause erection where impotence may exist due to these physiological conditions or due to psychological conditions. Likewise, the application of electrical stimulation to female genitalia can cause arousal when frigidity may exist due to these physiological conditions or due to psychological conditions. Indeed, it is known that the application of electrical stimulation to penile, vaginal, clitoral, anal, or prostate tissue can induce orgasm, even where the subject has suffered damage to the nerves serving the sex organs.

The art is replete with various devices used to apply electrical stimulation to the subject areas. Rigid rings capable of transmitting low levels of electricity to the skin and muscles are typically applied about the penis and/or the scrotum. Insertable rolled or plug-type electrodes, made to be rolled to size, or sized in a variety of sizes to fit the user's anatomy, are known for the purpose of applying low levels of electricity to the skin and muscles inside and surrounding the penis, the vagina, and the anus.

Rigid rings are useable for males where the application of electrical current to only a portion of penile tissue is sufficient to induce erection. However, due to the tremendously varying size of the penile tissue from rest to engorgement, the rigid ring may cause discomfort or pain to the user when the penis is engorged. In order to avoid this problem, the user may use a large diameter ring on a small diameter penis or change rings at some point prior to engorgement. Unfortunately, a rigid ring that is too large may not produce the desired affect and changing rings may be viewed as being too inconvenient. Furthermore, a rigid ring is not useable for females since the female genitalia are largely internal organs.

For both males and females, internally worn insertable electrodes are desirable to stimulate and to induce orgasm. However, many of these prior art insertable electrodes are difficult to retain in the appropriate position, uncomfortable for prolonged wear due to rigid components, and hard to effectively clean.

It would be highly advantageous, therefore, to remedy the foregoing and other deficiencies inherent in the prior art.

SUMMARY OF THE INVENTION

Accordingly, it is an object of the present invention to provide improvements in electrical stimulation apparatus for both men and women.

Another object of the invention is to provide improved means for the application of electrical stimulation to the penile, scrotal, anal, vaginal, and clitoral tissue.

Yet another object of the invention is to provide male stimulation apparatus that can induce erection and orgasm, and female electrical stimulation apparatus that can induce orgasm.

Yet another object of the invention is to provide means for the application of electrical stimulation to the penile tissue that is comfortable to wear during penile engorgement.

Yet another object of the invention is to provide improved means for disassembly of the electrical stimulation apparatus for cleaning.

The above and other advantages of the present invention are carried out in one form by an electrode apparatus which includes a flexible base having first and second sides and a hole running from the first side to the second side. An electrode is removably coupled to the flexible base. The electrode has a first section extending from the first side of the flexible base from the hole and a second section extending from the second side of the flexible base plate from the hole. An electrical contact is in electrical communication with the first section of the electrode, and an insulator surrounds the first section of the electrode and an end of the electrical contact.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
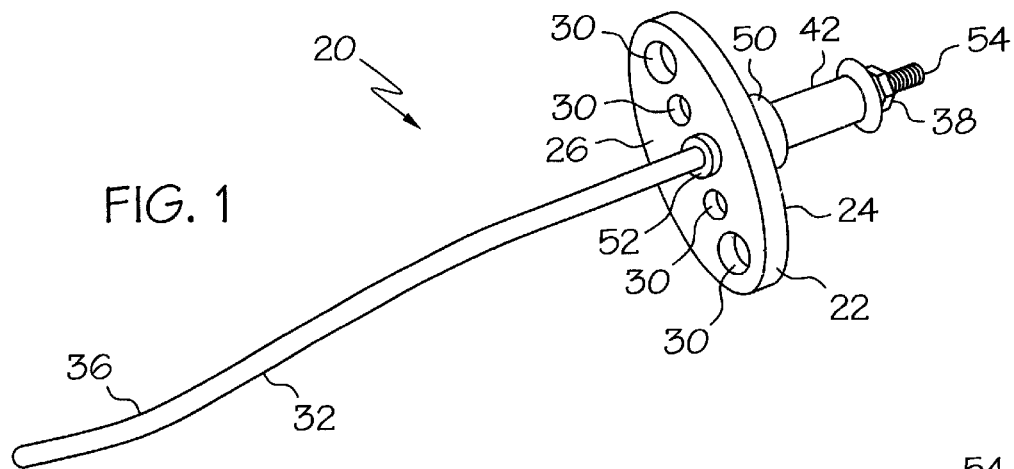
FIG. 1 shows a perspective view of an electrode apparatus in accordance with the present invention.
Figure 2:
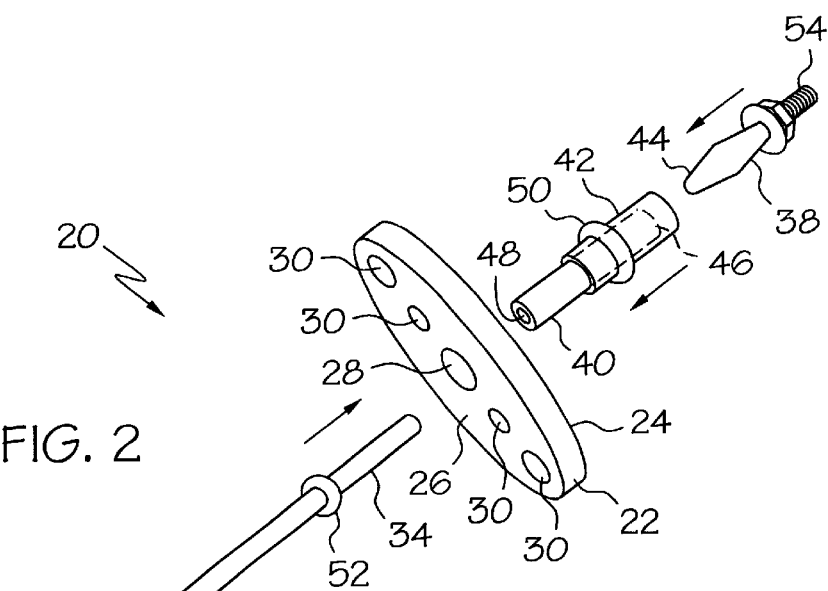
FIG. 2 shows an exploded perspective view of the electrode apparatus shown in FIG. 1.
Figure 3:
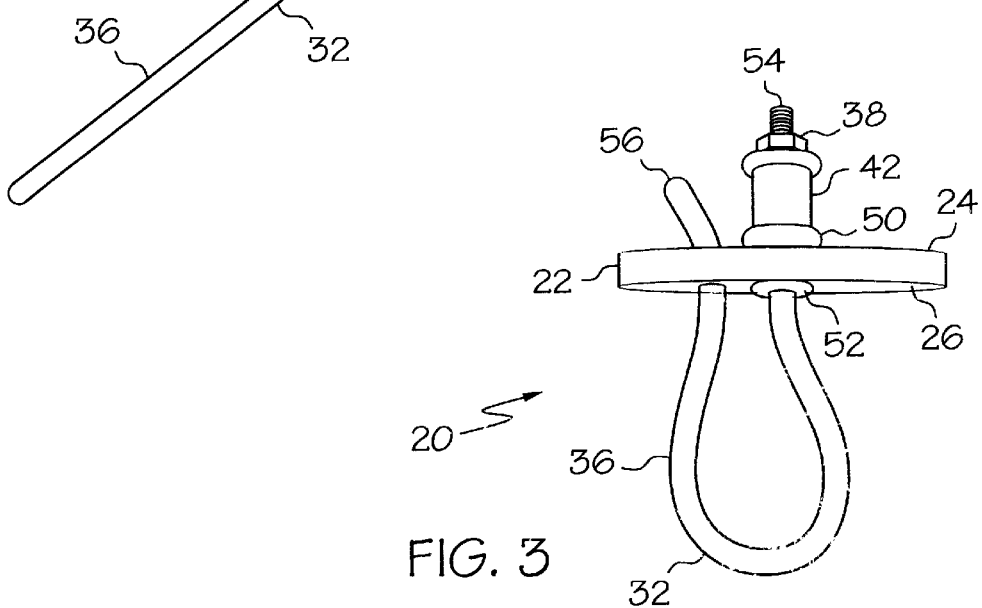
FIG. 3 shows a side view of the electrode apparatus shown in FIG. 1 arranged in a second configuration.

Turning now to the drawings in which like reference characters indicate corresponding elements throughout the several views, attention is first directed to FIGS. 1–3 where an electrode apparatus 20 is shown. FIG. 1 shows a perspective view of electrode apparatus 20 in accordance with the present invention. FIG. 2 shows an exploded perspective view of electrode apparatus 20. FIG. 3 shows a side view of electrode apparatus 20 arranged in a second configuration.

Electrode apparatus 20 includes a flexible base in the form of a base plate 22 which has a first side 24 and a second side 26. Extending therethrough base plate 22 is a first hole 28 and supplementary holes 30. Flexible base plate 22 is fabricated from an elastomeric material such as silicon, viton, or neoprene, such material being nonconductive, comfortable, and readily cleanable.

An electrode 32 is disposed through base plate 22 by inserting electrode 32 through first hole 28 such that a first section 34 of electrode 32 extends from first side 24 of base plate 22 and a second section 36 of electrode 32 extends from second side 26 of base plate 22. Electrode 32 is desirably fabricated from an elastomeric material such as silicon, viton, or neoprene for comfort and cleanability. Electrode 32 is flexible so that electrode 32 can adapt to the particular anatomy in which it will be inserted or upon which it will be worn. Electrode 32 is made conductive along the length of electrode 32 by embedding carbon particles in the elastomeric material during fabrication.

Electrode apparatus 20 further includes an electrical contact 38, a tube 40, and a insulator 42. With particular reference to FIG. 2, during assembly a first end 44 of electrical contact 38 plugs directly into a first tube end 46 of tube 40 (shown by hidden lines). Likewise, first section 34 of electrode 32 plugs directly into a second tube end 48 of tube 40. Tube 40 is fabricated from an elastomeric material and made conductive by embedded carbon particles so that tube 40 forms a path for electrical communication between electrical contact 38 and electrode 32.

Following the coupling of first end 44 and first section 34 of electrode 32 to tube 40, insulator 42 is positioned around tube 40 so that insulator 42 substantially surrounds tube 40. However, tube 40 is longer than insulator 42 so that second tube end 48 extends from insulator 42. Second tube end 48 is configured for press-fit into first hole 28 of flexible base plate 22.

In the preferred embodiment, insulator 42 is a flexible tube which is fabricated from an elastomeric material such as silicon, viton, or neoprene, such material being electrically-nonconductive, comfortable, and readily cleanable. In addition, insulator 42 carries an O-ring 50. O-ring 50 is slid along insulator 42 to rest against first side 24 of base plate 22 and serves to compressively secure insulator 42 on tube 40 in order to retain first section 34 of electrode 32 within tube 40.

During assembly, a second O-ring 52 is slid along electrode 32 to rest against second side 26 of base plate 22. Thus, base plate 22 is sandwiched between O-ring 50 and second O-ring 52 to substantially prevent movement of flexible base plate 22 relative to electrode 32. Electrode apparatus 20 is readily assembled and disassembled without the use of tools. In addition, the simplicity of the coupling between the components allows electrode apparatus 20 to be easily disassembled for cleaning and replacement of parts.

Once electrode apparatus 20 is assembled, a second end 54 of electrical contact 38 extends from insulator 42. Second end 54 conducts electricity to electrode 32 through first end 44 and tube 40 when second end 54 is connected to a source of electricity, typically a controller allowing for adjustment of current (not shown). The controller will typically include a jack, and a wire connected to the jack. The wire will typically terminate with a connector which is configured for attachment to second end 54. Such a connector is shown in FIG. 4.

Referring specifically to FIG. 3, electrode apparatus 20 is configured by inserting a third section 56 of electrode 32 adjoining second section 36 through one of supplementary holes 30 so that third section 56 extends from first side 24 of base plate 22. In this configuration, second section 36 forms a loop from first hole 28 to the one of supplementary holes 30 on second side 26 of base plate 22. The loop may be adjusted in size by either pushing or pulling third section 56 through any of supplementary holes 30 of base plate 22. Supplementary holes 30 may be sized to effectively retain electrode 32 by friction fit. Alternatively, an O-ring (not shown) may be slid along third section 56 to rest against first side 24 of base plate 22 thereby preventing the loop from increasing in length.

Thus, in the loop configuration, electrode apparatus 20 is particularly effective for causing erection or orgasm when the loop is tightened down around the penis or scrotal tissue. Furthermore, since the loop is easily adjustable and since electrode 32 is fabricated from flexible elastomeric material, electrode may be comfortably worn on the penis from rest through engorgement. The loop may also be inserted into vaginal or anal cavities for stimulation of the vaginal or anal tissue.

Figure 4:
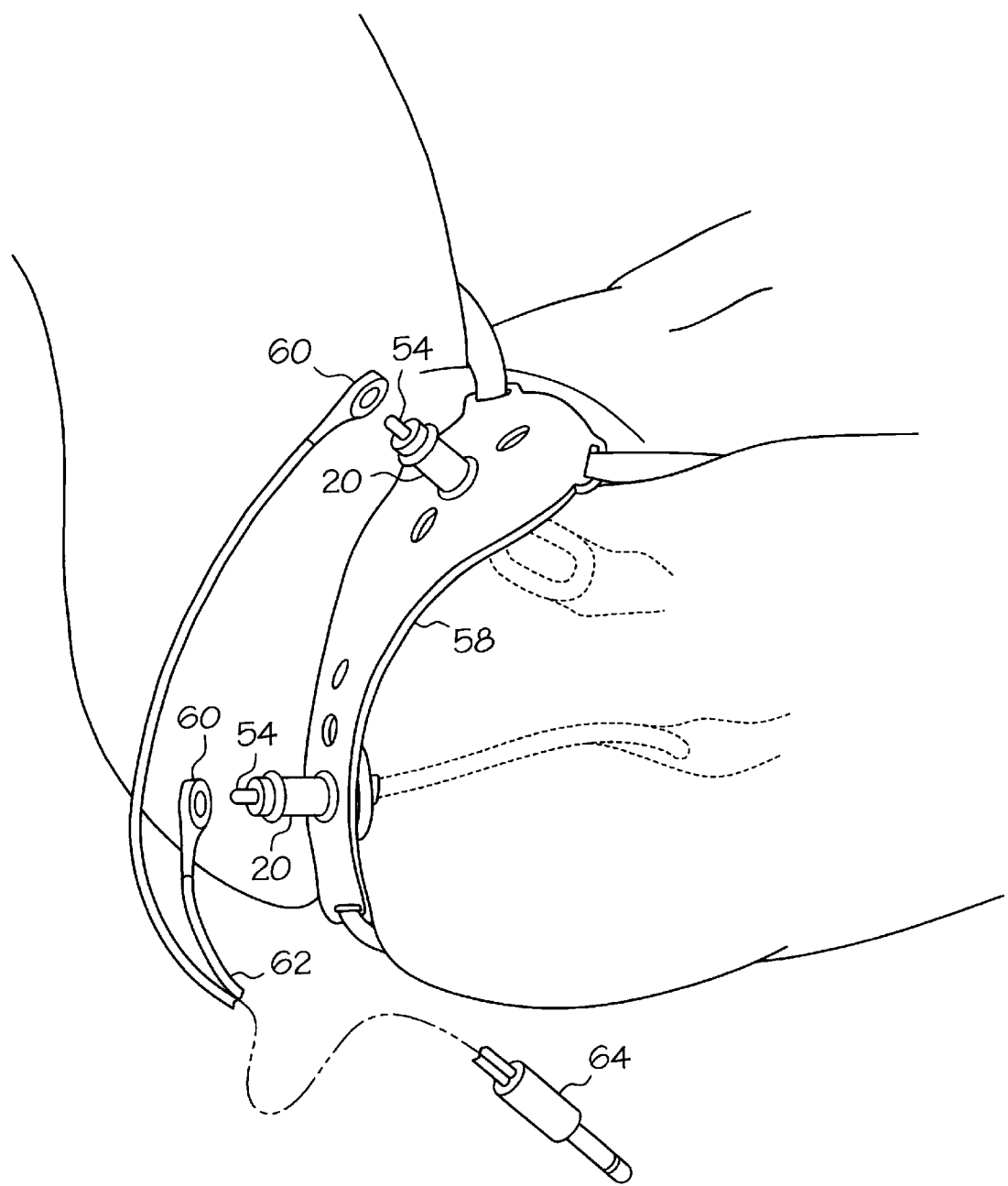
FIG. 4 shows the electrode apparatus in the configuration shown in FIG. 1 used in combination with another electrode apparatus in the configuration shown in FIG. 3.

FIG. 4 shows electrode apparatus 20 in the configuration shown in FIG. 1 used in combination with another electrode apparatus 20 in the configuration shown in FIG. 3. Each of electrode apparatuses 20 are retained by a flexible plate and belt system 58 which securely retains electrode apparatuses 20 near the female genitalia. In this view, the looped configuration of electrode apparatus 20 shown in FIG. 3 is placed vaginally and the configuration of electrode apparatus 20 shown in FIG. 1 is placed anally. Connectors 60 may be attached to their respective second ends 54 on each of electrode apparatuses 20. Running directly to and connected to connectors 60 is a conductive line 62. Line 62 has a plug connector 64 which connects electrode apparatuses 20 to an electrical supply box (not shown).

Figure 5:
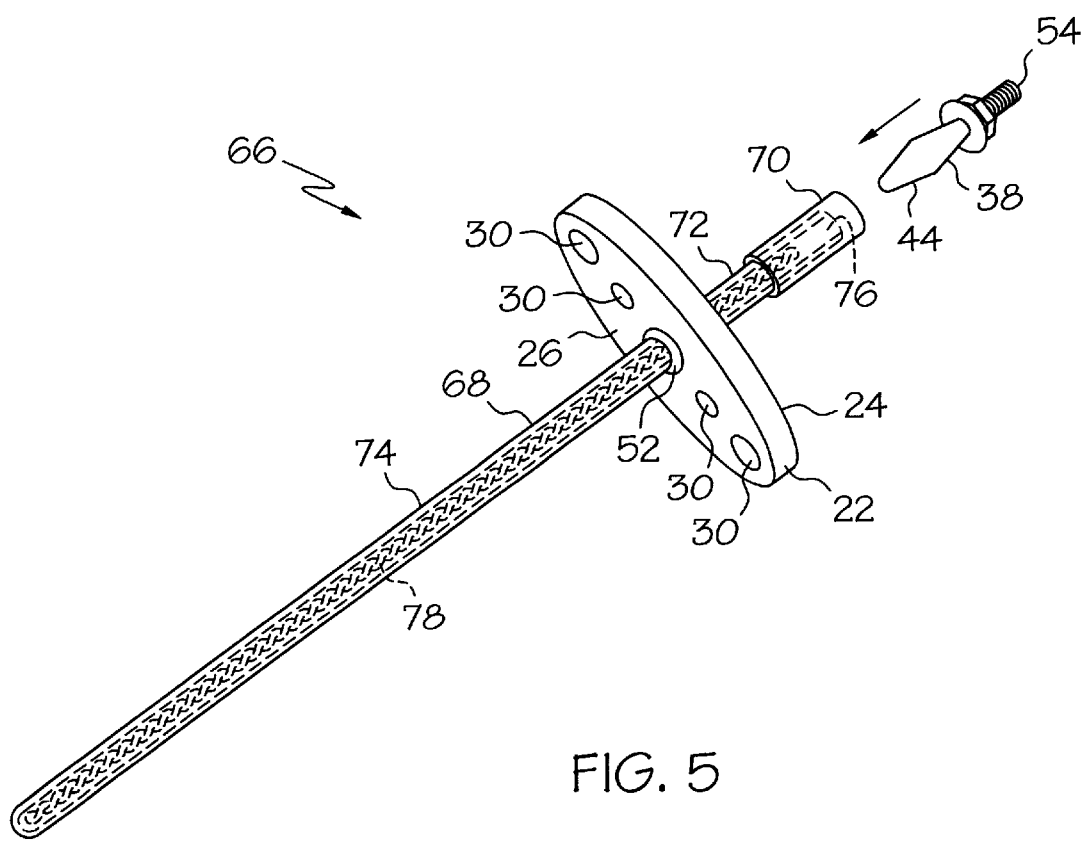
FIG. 5 shows a perspective view of an alternative electrode apparatus in accordance with the present invention.

FIG. 5 shows a perspective view of an alternative electrode apparatus 66 in accordance with the present invention. Electrode apparatus 66 includes base plate 22 and electrical contact 38, both of which have been described above. Electrode apparatus 66 also includes an electrode 68 and an electrically-nonconductive insulator in the form of a tube 70. Electrode 68 is disposed through base plate 22 by inserting electrode 68 through first hole 28 (FIG. 2) such that a first section 72 of electrode 68 extends from first side 24 of base plate 22 and a second section 74 of electrode 68 extends from second side 26 of base plate 22. Electrode 68 is formed from flexible elastomeric material made electrically-conductive along its length by embedded carbon particles. Electrode 68 has an internal longitudinal passage 76 along the length of electrode 68. A deformable wire 78 is located in and axially aligned with internal longitudinal passage 76.

During assembly, tube 70 is slid over first section 72. First end 44 of electrical contact 38 is then plugged directly into internal longitudinal passage 76 at the end of first section 76 so that first end 44 extends into internal longitudinal passage 76 and second end 54 extends from the end of first section 72 of electrode 68. First end 44 is retained in internal longitudinal passage 76 through friction fit. Base plate 22 is positioned on electrode 68 to fit against tube 70. Optionally, O-ring 50 (FIG. 2) may be slid over tube 70 and O-ring 52 may be slid onto electrode 68 thereby substantially preventing base plate 22 from moving relative to electrode 68. Thus, electrode apparatus 66 is readily assembled and disassembled for cleaning and/or replacement of components.

Deformable wire 72 has the ability to hold electrode 68 in a formed shape following deformation from an original shape. In the preferred embodiment, the original shape of electrode 68 is approximately straight. Thus, wire 72 allows electrode 68 to be bent and retained in the bent posture for more effective and comfortable placement.

Figure 6:
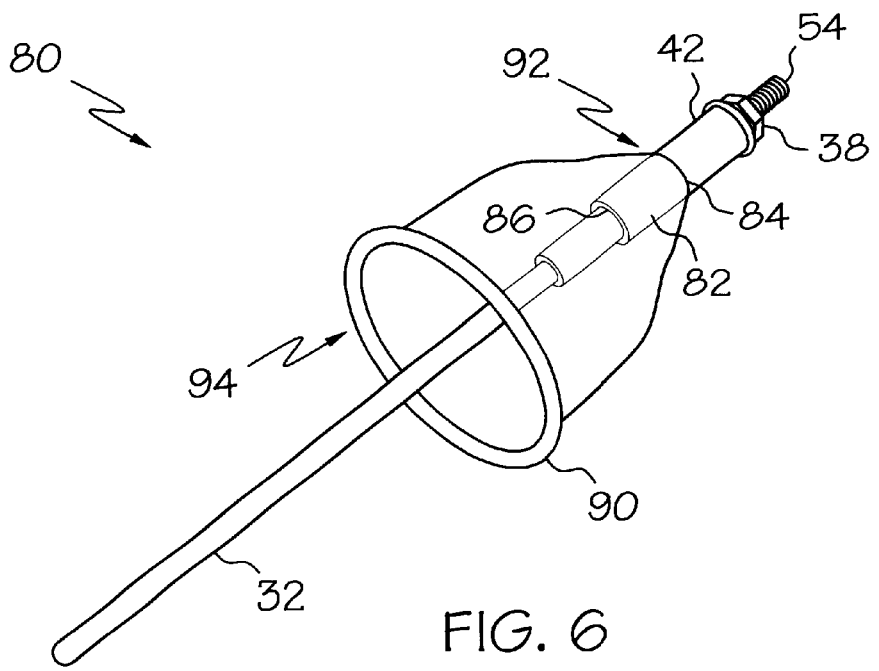
FIG. 6 shows a perspective view of a third electrode apparatus designed for penile use.
Figure 7:
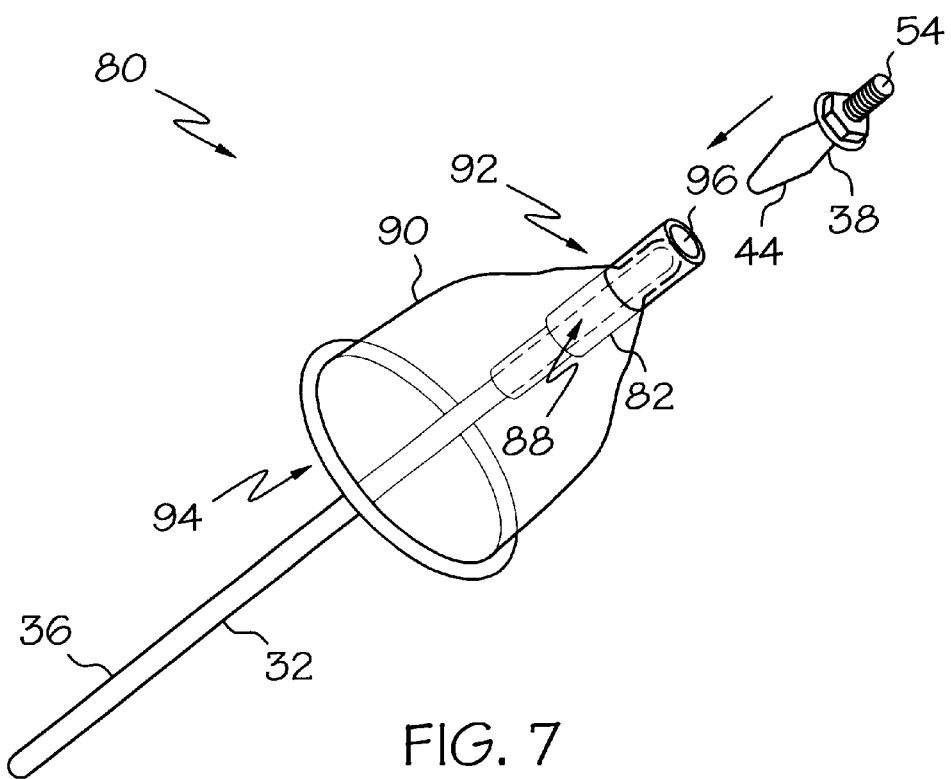
FIG. 7 shows a partially exploded perspective view of the assembly of the third electrode apparatus.

Referring to FIGS. 6 and 7, FIG. 6 shows a perspective view of a third electrode apparatus 80 designed for penile use in accordance with the present invention. FIG. 7 shows a partially exploded perspective view of the assembly of third electrode apparatus 80. Electrode apparatus 80 includes tube 40, insulator 42 (see FIG. 2), electrode 32, and electrical contact 38 having first and second ends 44 and 54, respectively, all of which have been described in detail in connection with electrode apparatus 20 (FIG. 1–3).

Electrode apparatus 80 has a flexible base in the form of a tubular base 82 having a first side 84, a second side 86, and a hole 88 running from first side 84 to second side 86. In this third embodiment of the present invention, electrode apparatus 80 further includes a penile sheath 90, which may desirably be a conventional condom, juxtaposed between insulator 42 and base 82. Penile sheath 90 has a substantially closed end 92 and an open end 94.

Referring particularly to FIGS. 2 and 7, during assembly penile sheath 90 is positioned over tube 40 such that open end 94 is directed toward second section 36 of electrode 32. Insulator 42 is then slid over tube 40 such that closed end 92 of penile sheath 90 is located between insulator 42 and tube 40, and envelopes tube 40. When first end 44 of electrical contact 38 is plugged into tube 40, as described in connection with electrode apparatus 20, first end 44 punctures penile sheath 90 to form an opening 96 on substantially closed end 92 so that first end 44 is in electrical communication with tube 40 and subsequently with first section 34 of electrode 32.

Penile sheath 90 allows electrode apparatus 80 to be worn on a penis so that electrode 32 lies along a length of the penis. In this configuration, electrode apparatus 80 is particularly effective at causing erection and orgasm. In addition, electrode apparatus 80 is readily assembled and disassembled for cleaning and replacement of components, especially for replacement of penile sheath 90 following orgasm.

Electrode apparatus 80 has been described in connection with electrode 32 and the assembly technique of electrode apparatus 20. However, it should be readily apparent that electrode apparatus 80 may include electrode 68, in which case, the assembly technique of electrode apparatus 66 applies.

Figure 8:
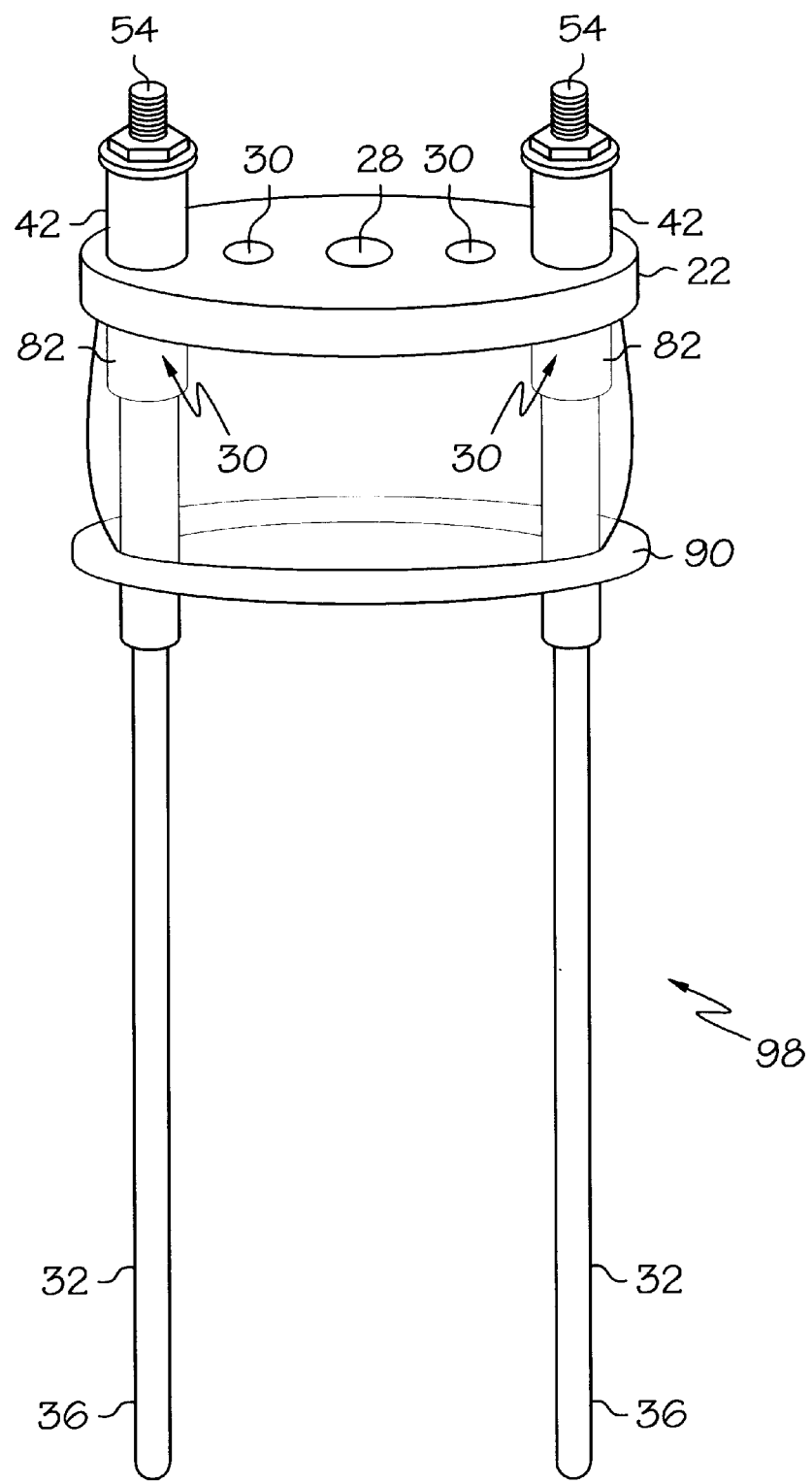
FIG. 8 shows a perspective view of a fourth electrode apparatus designed for penile use.
Figure 9:
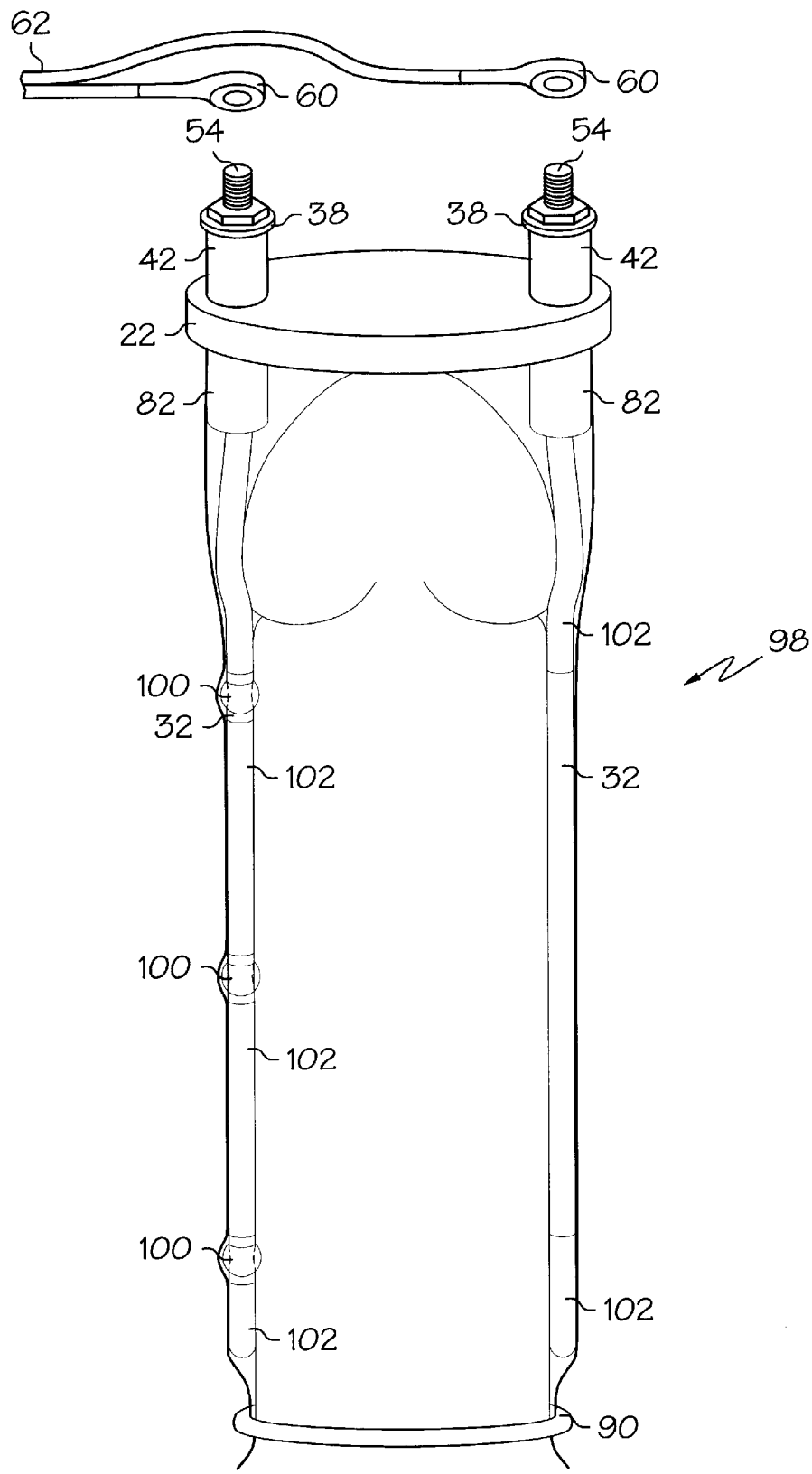
FIG. 9 shows the fourth electrode apparatus of FIG. 8 in use.

Referring to FIGS. 8–9, FIG. 8 shows a perspective view of a fourth electrode apparatus 98 designed for penile use and FIG. 9 shows electrode apparatus 98 positioned on a penis. Electrode apparatus 98 combines the elements of electrode apparatus 20 (FIG. 1) and electrode apparatus 80 (FIG. 6) to form an electrode device which includes two electrodes 32 spatially positioned relative to one another.

Electrode apparatus 98 includes penile sheath 90 positioned between each of two tubular flexible bases 82 and base plate 22. In the preferred embodiment of electrode apparatus 98, electrodes 32 are directed through two of supplementary holes 30 on base plate 22. In this configuration electrode apparatus 98 allows both of electrodes 32 to lie along a length of the penis as specifically shown in FIG. 9.

Also shown in FIG. 9, electrode apparatus 98 optionally includes electrically-conductive beads 100 and electrically-nonconductive covers 102. Beads 100 and covers 102 are removably coupled and slidable along the length of second section 36 of electrodes 32. Covers 102 may be selectively positioned to insulate particular areas of the penis from electrical stimulation. Conversely, beads 100 may be selectively positioned to impart a concentrated electrical stimulus to a particular area of the penis. In particular, as shown in FIG. 9, one of beads 100 may be positioned between two covers 102 so that a specific region on the penis is electrically stimulated without stimulating the areas immediately adjacent to the contact area of the one of beads 100.

Although beads 100 and covers 102 are described in connection with electrodes 32 used with electrode apparatus 98, it should be readily apparent to those skilled in the art that beads 100 and covers 102 may be incorporated on electrode 32 of electrode apparatus 20 (FIG. 2) and on electrode 68 (FIG. 5) of electrode apparatus 66 (FIG. 5) as well.

In summary, the present invention provides an electrical stimulation apparatus that may be adapted for use by both men and women to induce erection and/or orgasm. Electrical stimulation may be applied to the penile, scrotal, anal, vaginal, and clitoral tissue by means of an electrode that can be configured to be substantially straight or formed and held in an adjustably sizable loop configuration. Alternatively, the electrode includes an embedded memory bend wire so that the electrode may be bent and held in the bent position to effectively accommodate vaginal or anal placement. Furthermore, an electrode apparatus is provided that includes a penile sheath for securely and comfortably retaining the device on a penis. Furthermore, the electrode apparatus and its various embodiments are readily assembled and disassembled for cleaning, replacement of components, and reconfiguration.

Although the preferred embodiments of the invention have been illustrated and described in detail, it will be readily apparent to those skilled in the art that various modifications may be made therein without departing from the spirit of the invention or from the scope of the appended claims.

What is claimed is:

1. An electrode apparatus comprising:
    a flexible base having first and second sides and first and second holes running from said first side to said second side;
    an electrode removably coupled to said flexible base, said electrode having first, second, and third sections, said first section extending from said first side of said flexible base from said first hole, said second section extending from said second side of said flexible base from said first hole, and said third section adjoining said second section, said third section extending from said first side of said base from said second hole so that said second section forms a loop from said first hole to said second hole on said second side of said flexible base;
    an electrical contact in electrical communication with said first section of said electrode; and
    an insulator surrounding said first section and an end of said electrical contact.

2. An electrode apparatus comprising:
    a flexible base having first and second sides and a hole running from said first side to said second side;
    an electrode removably coupled to said flexible base, said electrode having first and second sections, said first section extending from said first side of said flexible base from said hole, and said second section extending from said second side of said flexible base from said hole;
    an electrical contact in electrical communication with said first section of said electrode;
    an insulator surrounding said first section and an end of said electrical contact; and
    a tube having first and second tube ends, said tube being conductive of electrical current, wherein:
        said end of said electrical contact plugs directly into said first tube end;

said first section of said electrode plugs directly into said second tube end; and said insulator surrounds said tube.

3. An electrode apparatus as claimed in claim 2 wherein said second tube end extends from said insulator and said second tube end is configured for press-fit into said hole of said flexible base.

4. An electrode apparatus comprising:

a flexible base having first and second sides and a hole running from said first side to said second side;

an electrode removably coupled to said flexible base, said electrode having first and second sections, said first section extending from said first side of said flexible base from said hole, and said second section extending from said second side of said flexible base from said hole;

an electrical contact in electrical communication with said first section of said electrode;

an insulator surrounding said first section and an end of said electrical contact, said insulator carrying an O-ring for compressively securing said insulator with said first section of said electrode.

5. An electrode apparatus comprising:

a flexible base having first and second sides and a hole running from said first side to said second side;

an electrode removably coupled to said flexible base, said electrode having first and second sections, said first section extending from said first side of said flexible base from said hole, and said second section extending from said second side of said flexible base from said hole;

an electrical contact in electrical communication with said first section of said electrode;

an insulator surrounding said first section and an end of said electrical contact; and a penile sheath overlapping said electrode, said penile sheath having a substantially closed end and an open end wherein:

said substantially closed end has an opening located proximate said first section through which an end of said electrical contact extends for allowing communication of electrical current to said first section; and said open end is directed toward said second section such that said penile sheath substantially surrounds said second section when said penile sheath is extended.

6. An electrode apparatus as claimed in claim 5 wherein said end of said electrical contact is configured to puncture said substantially closed end to form said opening when said end is positioned in said insulator.

7. An electrode apparatus comprising:

a flexible base having first and second sides and a hole running from said first side to said second side;

an electrode removably coupled to said flexible base, said electrode having first and second sections, said first section extending from said first side of said flexible base from said hole, and said second section extending from said second side of said flexible base from said hole, said electrode having an internal longitudinal passage along a length of said electrode;

a wire located in and axially aligned with said internal longitudinal passage;

an electrical contact in electrical communication with said first section of said electrode; and an insulator surrounding said first section and an end of said electrical contact.

8. An electrode apparatus as claimed in claim 7 wherein said wire is configured to hold said electrode in a formed shape following deformation from an original shape.

9. An electrode apparatus as claimed in claim 7 wherein said end of said electrical contact plugs directly into said internal longitudinal passage in said first section and a second end of said electrical contact extends from said first section of said electrode.

10. An electrode apparatus comprising:

a first flexible base having first and second sides and a first hole running from said first side to said second side;

a first electrode removably coupled to said first flexible base, said first electrode having first and second sections, said first section extending from said first side of said first flexible base from said first hole, and said second section extending from said second side of said first flexible base from said first hole;

a first electrical contact in electrical communication with said first section of said first electrode;

a first insulator surrounding said first section and an end of said first electrical contact;

a second flexible base having third and fourth sides and a second hole running from said third side to said fourth side;

a second electrode removably coupled to said second flexible base, said second electrode having third and fourth sections, said third section extending from said third side of said second flexible base from said second hole, and said fourth section extending from said fourth side of said second flexible base from said second hole;

a second electrical contact in electrical communication with said third section of said second electrode;

a second insulator surrounding said third section and a second end of said second electrical contact; and a flexible plate having a third hole through which said first section of said first electrode extends and a fourth hole through which said third section of said second electrode extends, said flexible plate retaining each of said first and second electrodes in a fixed relationship relative to one another.

11. An apparatus as claimed in claim 10 wherein said first and second electrodes are removably coupled to said flexible plate.

12. An electrode apparatus comprising:

a flexible base having first and second sides and a hole running from said first side to said second side;

an electrode removably coupled to said flexible base, said electrode having first and second sections, said first section extending from said first side of said flexible base from said hole, and said second section extending from said second side of said flexible base from said hole, said electrode being conductive of electrical current along a length of said electrode;

covers removably coupled to said second section of said electrode, said covers being nonconductive of electrical current;

an electrical contact in electrical communication with said first section of said electrode; and an insulator surrounding said first section and an end of said electrical contact.

13. An electrode apparatus as claimed in claim 12 further comprising at least one electrically-conductive bead removably coupled to said second section of said electrode, said bead being slidably adjustable along a length of said second section, and said bead being positioned between two of said covers.

14. An electrode apparatus comprising:
- a flexible base having first and second sides and first and second holes running from said first side to said second side;
- an electrode removably coupled to said flexible base, said electrode having first, second, and third sections, said first section extending from said first side of said flexible base from said first hole, said second section extending from said second side of said flexible base from said first hole to said second hole to form a loop, and said third section extending from said first side of said base from said second hole;
- an electrical contact having a first end and a second end, said first end being in electrical communication with said first section of said electrode;
- an insulator surrounding said first section and said first end;
- a first O-ring mounted on said electrode for substantially preventing movement of said flexible base relative to said electrode; and
- a second O-ring mounted on said insulator for compressively securing said insulator with said first section of said electrode.

15. An electrode apparatus as claimed in claim 14 additionally comprising a tube having first and second tube ends, said tube being conductive of electrical current, wherein:
- said end of said electrical contact plugs directly into said first tube end;
- said first section of said electrode plugs directly into said second tube end; and
- said insulator surrounds said tube.

16. An electrode apparatus as claimed in claim 14 wherein:
- said electrode has an internal longitudinal passage along a length of said electrode, said end of said electrical contact plugging directly into said internal longitudinal passage in said first section and said second end of said electrical contact extending from said first section of said electrode; and
- said apparatus further comprises a wire located in and axially aligned with said internal longitudinal passage, said wire being configured to hold said electrode in a formed shape following deformation from an original shape.

17. An electrode apparatus comprising:
- a first flexible base having first and second sides and a first hole running from said first side to said second side;
- a first electrode removably coupled to said first flexible base, said first electrode having first and second sections, said first section extending from said first side of said first flexible base from said first hole, and said second section extending from said second side of said first flexible base from said first hole;
- a first electrical contact in electrical communication with said first section of said first electrode;
- a first insulator surrounding said first section and an end of said first electrical contact;
- a second flexible base having third and fourth sides and a second hole running from said third side to said fourth side;
- a second electrode removably coupled to said second flexible base, said second electrode having third and fourth sections, said third section extending from said third side of said second flexible base from said second hole, and said fourth section extending from said fourth side of said second flexible base from said second hole;
- a second electrical contact in electrical communication with said third section of said second electrode;
- a second insulator surrounding said third section and an end of said second electrical contact;
- a flexible plate having a third hole through which said first section of said first electrode extends and a fourth hole through which said third section of said second electrode extends, said flexible plate retaining each of said first and second electrodes in a fixed relationship relative to one another; and
- a penile sheath overlapping said first and second electrodes, said penile sheath having a substantially closed end and an open end wherein:
    - said substantially closed end has a first opening located proximate said first section through which said end of said first electrical contact extends and a second opening located proximate said third section through which said end of said second electrical contacts extends; and
    - said open end is directed toward said second and fourth sections such that said penile sheath substantially surrounds said second and fourth sections when said penile sheath is extended.

* * * * *